United States Patent [19]

Rogow

[11] Patent Number: 5,878,909
[45] Date of Patent: Mar. 9, 1999

[54] GLOVE DISPENSER

[76] Inventor: Mark R. Rogow, 3408 Bertha Dr., Baldwin, N.Y. 11510

[21] Appl. No.: 769,760

[22] Filed: Dec. 20, 1996

[51] Int. Cl.⁶ ..................................................... B65H 1/00
[52] U.S. Cl. .................................. 221/45; 221/289; 312/1
[58] Field of Search ................................. 221/27, 28, 29, 221/33, 34, 45, 289, 290, 294, 298, 210; 312/1, 3, 4, 5

[56] References Cited

U.S. PATENT DOCUMENTS

| 4,228,935 | 10/1980 | Madray | 223/111 |
| 4,677,697 | 7/1987 | Hayes | 2/159 |
| 4,773,532 | 9/1988 | Stephenson | 206/278 |
| 5,570,808 | 11/1996 | Tassoni | 221/34 |

FOREIGN PATENT DOCUMENTS

| 4126511A | 2/1992 | Germany | 221/33 |

Primary Examiner—David A. Bucci
Assistant Examiner—Thuy V. Tran

[57] ABSTRACT

A glove dispenser including a glove dispensing housing. Further provided is a plurality of rods extending between side faces of the housing. A pair of gloves are releasably coupled adjacent an opening thereof between each rod. Finally, a dispensing mechanism is situated within the housing for allowing the dispensing of the gloves.

6 Claims, 4 Drawing Sheets

GLOVE DISPENSER

BACKGROUND OF THE INVENTION

1. Field of the Invention

The present invention relates to a glove dispenser and more particularly pertains to automatically dispensing a plurality of gloves with a self-powered glove dispenser.

2. Description of the Prior Art

The use of glove dispensers is known in the prior art. More specifically, glove dispensers heretofore devised and utilized for the purpose of dispensing gloves are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 4,909,413 to McCutcheon; U.S. Pat. No. 4,951,815 to Ulbrich; U.S. Pat. Des. No. 299,686 to Jonas et al.; U.S. Pat. No. 4,844,293 McLaughlin; U.S. Pat. No. 4,773,532 to Stephenson; and U.S. Pat. No. 5,088,620 to Kelliher et al.

In this respect, the glove dispenser according to the present invention substantially departs from the conventional concepts and designs of the prior art, and in so doing provides an apparatus primarily developed for the purpose of automatically dispensing a plurality of gloves with a self-powered glove dispenser.

Therefore, it can be appreciated that there exists a continuing need for a new and improved glove dispenser which can be used for automatically dispensing a plurality of gloves with a self-powered glove dispenser. In this regard, the present invention substantially fulfills this need.

SUMMARY OF THE INVENTION

In view of the foregoing disadvantages inherent in the known types of glove dispensers now present in the prior art, the present invention provides an improved glove dispenser. As such, the general purpose of the present invention, which will be described subsequently in greater detail, is to provide a new and improved glove dispenser which has all the advantages of the prior art and none of the disadvantages.

To attain this, the present invention essentially comprises a glove dispensing housing with a rectilinear configuration. The housing has a front face, a rear face, a bottom face, a top opening, and a pair of side faces defining an interior space. As shown in FIGS. 2–3, the housing further has a first divider comprising an inner peripheral lip extending inwardly from the front face, the rear face, and the side faces of the housing. Such first divider subdivides the interior space of the housing and defines an upper compartment. The upper compartment has a pair of aligned vertical slots formed in the side faces of the housing adjacent the front face thereof. With reference still to 2–3, the housing further includes a second divider comprising a planar horizontally oriented plate situated below the first divider. The second divider thus defines an intermediate compartment between the first divider and the second divider and further defines a lower compartment situated between the second divider and the bottom face of the housing. The intermediate compartment has a pair of angled slots formed in the side faces of the housing. See FIG. 2. It is imperative that the angle slots be in communication at a top end thereof with the vertical slots. A horizontal slot is formed in the second divider between the angled slots to allow access to the lower compartment from the intermediate compartment. A pair of circular cut outs are formed in the front face of the housing and oriented side by side. Associated therewith is a pair of horizontally oriented guide tubes integrally coupled to the housing. The guide tubes are oriented such that each tube has a first opening situated coincidentally in axial alignment with an associated circular cut out and a second opening situated in communication with the intermediate compartment. For reasons that with become apparent hereinafter, each guide tube has a slot formed about a periphery thereof in constant alignment with the angle slots of the intermediate compartment. The lower compartment has a pair of aligned rectangular cut outs formed in opposite side faces of the housing adjacent the bottom face thereof. As shown in FIG. 2, the rectangular cut outs are in communication with a bottom end of both of the angled slots of the intermediate compartment. As shown in FIGS. 7 & 8, a disposable multiple glove assembly is includes with a rectilinear configuration. The disposable multiple glove assembly has a top face, a front face, a rear face, and a pair of side faces defining an interior space with a bottom opening. The side faces have a pair of slots formed therein adjacent the front face of the assembly. The disposable multiple glove assembly further includes a plurality of rods extending between the slots of the assembly. For precluding lateral movement of the rods within the slots, each is equipped with a flange on both ends thereof. The disposable multiple glove assembly further includes a pair of gloves releasably coupled adjacent an opening thereof between each rod. By this structure, the disposable multiple glove assembly may be inserted within the upper compartment of the housing with the flanges of the rods residing within the vertical slots of the upper compartment. Finally, a dispensing mechanism is provided for allowing the gloves to be dispensed. As best shown in FIG. 4, the dispensing mechanism includes a first flexible tab coupled at a first end thereof to the peripheral lip of the first divider. The first flexible tab extends inwardly therefrom between a bottom of the vertical slots of the upper compartment of the housing. In operation, the first flexible tab is adapted be biased downwardly. The dispensing mechanism further includes a second flexible tab coupled at a first end thereof to the plate of the second divider adjacent the horizontal slot thereof. Such second divider extends from the point of coupling to a position between a bottom of the angled slots of the intermediate compartment of the housing. The second flexible tab is adapted be biased only downwardly in use. By this structure, a lowermost rod of the disposable multiple glove assembly may be situated below the second flexible tab before use. Further, a second lowermost rod may be situated above the first tab such that the openings of the associated pair of gloves are positioned in alignment with the second ends of the guide tubes.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved glove dispenser which has all the advantages of the prior art glove dispensers and none of the disadvantages.

It is another object of the present invention to provide a new and improved glove dispenser which may be easily and efficiently manufactured and marketed.

It is a further object of the present invention to provide a new and improved glove dispenser which is of a durable and reliable construction.

An even further object of the present invention is to provide a new and improved glove dispenser which is susceptible of a low cost of manufacture with regard to both materials and labor, and which accordingly is then susceptible of low prices of sale to the consuming public, thereby making such glove dispenser economically available to the buying public.

Still yet another object of the present invention is to provide a new and improved glove dispenser which provides in the apparatuses and methods of the prior art some of the advantages thereof, while simultaneously overcoming some of the disadvantages normally associated therewith.

Still another object of the present invention is to automatically dispense a plurality of gloves with a self-powered glove dispenser.

Lastly, it is an object of the present invention to provide a new and improved glove dispenser including a glove dispensing housing. Further provided is a plurality of rods extending between side faces of the housing. A pair of gloves are releasably coupled adjacent an opening thereof between each rod. Finally, a dispensing mechanism is situated within the housing for allowing the dispensing of the gloves.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
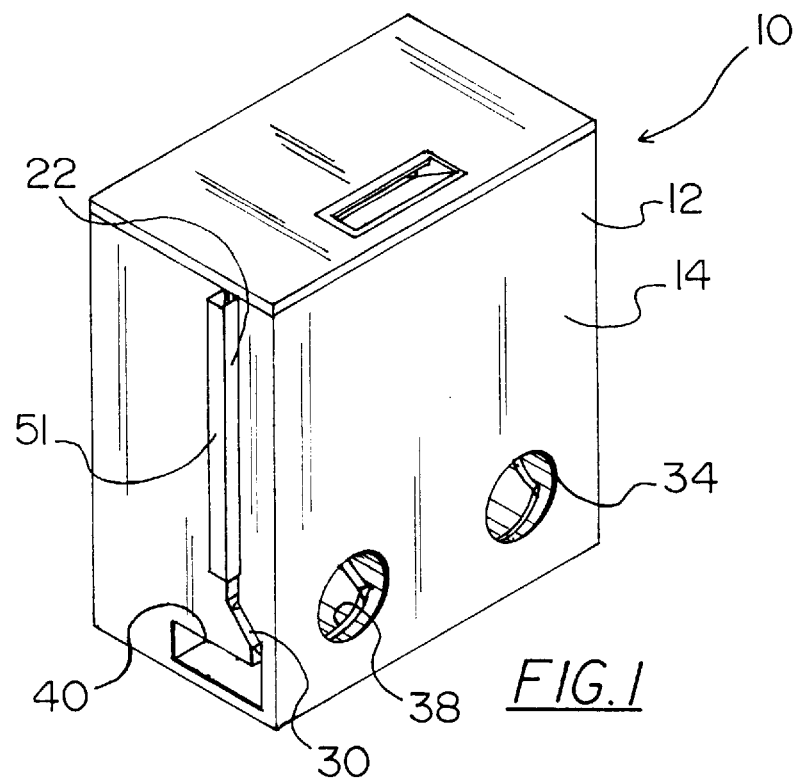
FIG. 1 is a perspective illustration of the preferred embodiment of the glove dispenser constructed in accordance with the principles of the present invention.

With reference now to the drawings, and in particular to FIG. 1 thereof, a new and improved glove dispenser embodying the principles and concepts of the present invention and generally designated by the reference numeral 10 will be described.

The present invention, the new and improved glove dispenser, is comprised of a plurality of components. Such components in their broadest context include glove dispensing housing, disposable multiple glove assembly, and dispensing mechanism. Such components are individually configured and correlated with respect to each other so as to attain the desired objective.

Figure 2:
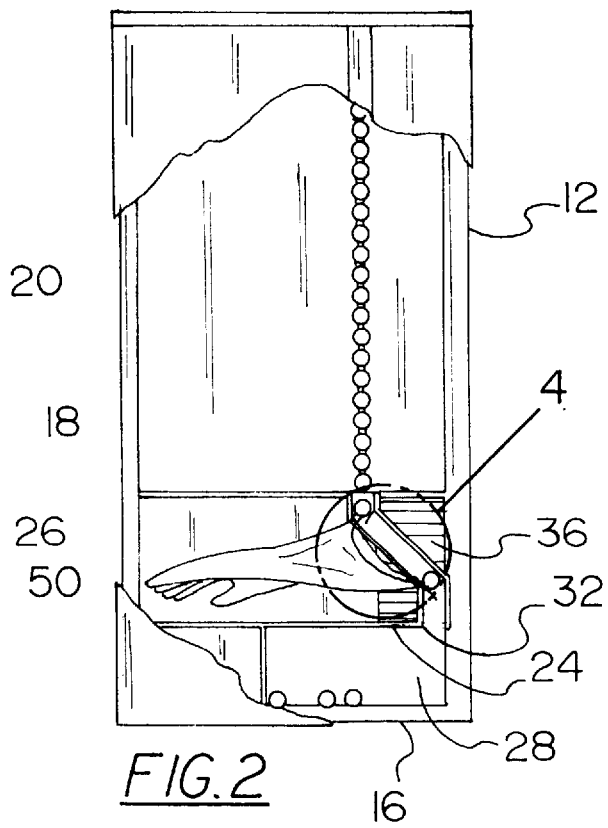
FIG. 2 is a side cut away view of the interior space of the housing.
Figure 3:
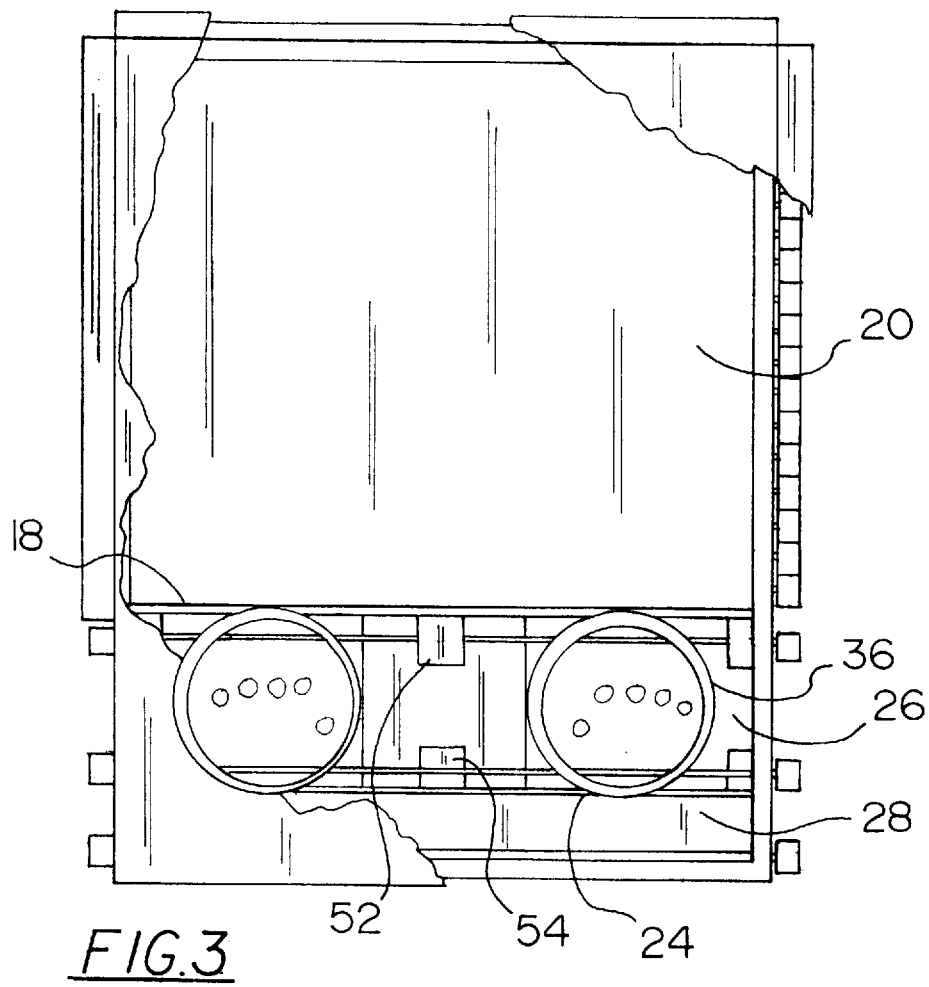
FIG. 3 is a front cut away view of the interior space of the housing.

More specifically, it will be noted that the system 10 of the present invention includes a glove dispensing housing 12 with a rectilinear configuration. The housing has a front face 14, a rear face, a bottom face 16, a top opening, and a pair of side faces defining an interior space. As shown in FIG. 1, a lid with a handle may be included for selectively closing the top opening. As shown in FIGS. 2–3, the housing further has a first divider 18 comprising an inner peripheral lip extending inwardly from the front face, the rear face, and the side faces of the housing. Such first divider subdivides the interior space of the housing and defines an upper compartment 20. The upper compartment has a pair of aligned vertical slots 22 formed in the side faces of the housing adjacent the front face thereof.

With reference still to FIGS. 2–3, the housing further includes a second divider 24 comprising a planar horizontally oriented plate situated below the first divider. The second divider thus defines an intermediate compartment 26 between the first divider and the second divider and further defines a lower compartment 28 situated between the second divider and the bottom face of the housing. The intermediate compartment has a pair of angled slots 30 formed in the side faces of the housing. See FIG. 2. It is imperative that the angle slots be in communication at a top end thereof with the vertical slots. A horizontal slot 32 is formed in the second divider between the angled slots to allow access to the lower compartment from the intermediate compartment. A pair of circular cut outs 34 are formed in the front face of the housing and oriented side by side. Associated therewith is a pair of horizontally oriented guide tubes 36 integrally coupled to the housing. The guide tubes are oriented such that each tube has a first opening situated coincidentally in axial alignment with an associated circular cut out and a second opening situated in communication with the intermediate compartment. For reasons that will become apparent hereinafter, each guide tube has a slot 38 formed about a periphery thereof in constant alignment with the angle slots of the intermediate compartment.

The lower compartment has a pair of aligned rectangular cut outs 40 formed in opposite side faces of the housing adjacent the bottom face thereof. As shown in FIG. 2, the rectangular cut outs are in communication with a bottom end of both of the angled slots of the intermediate compartment.

Figure 5:
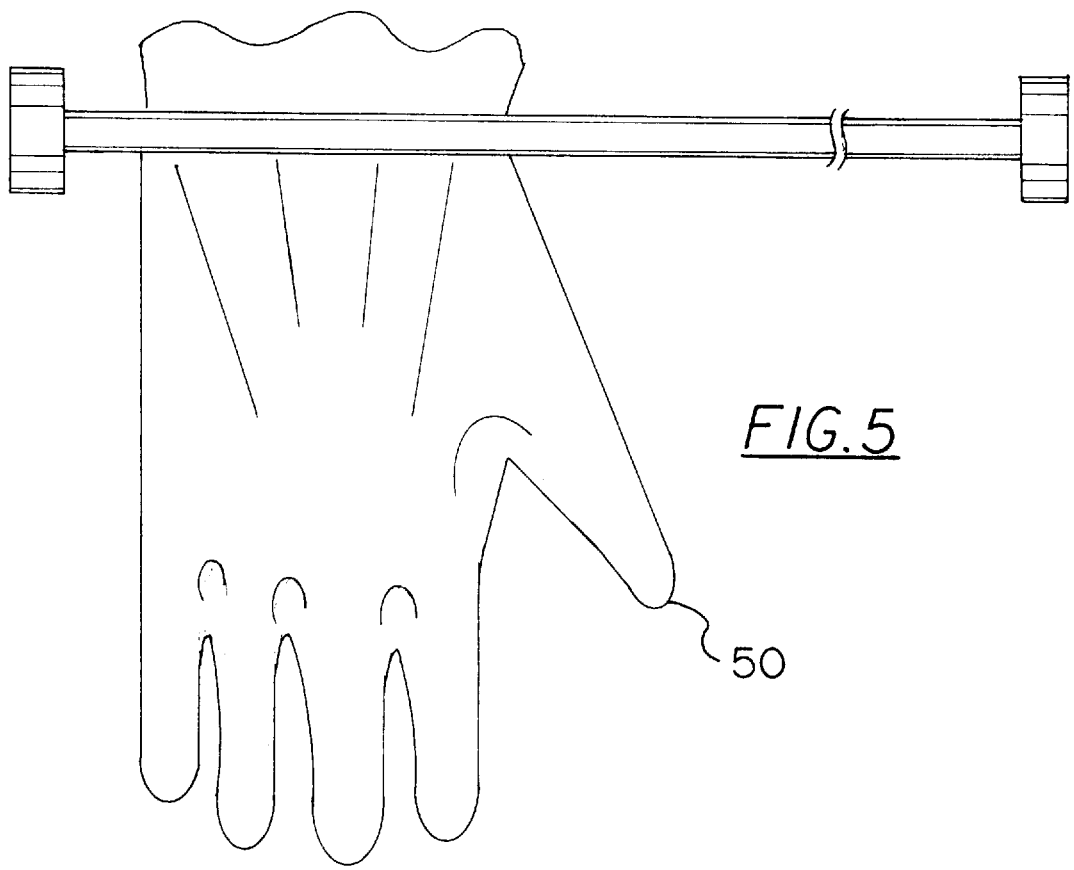
FIG. 5 is a top view of one of the gloves and associated rod.
Figure 6:
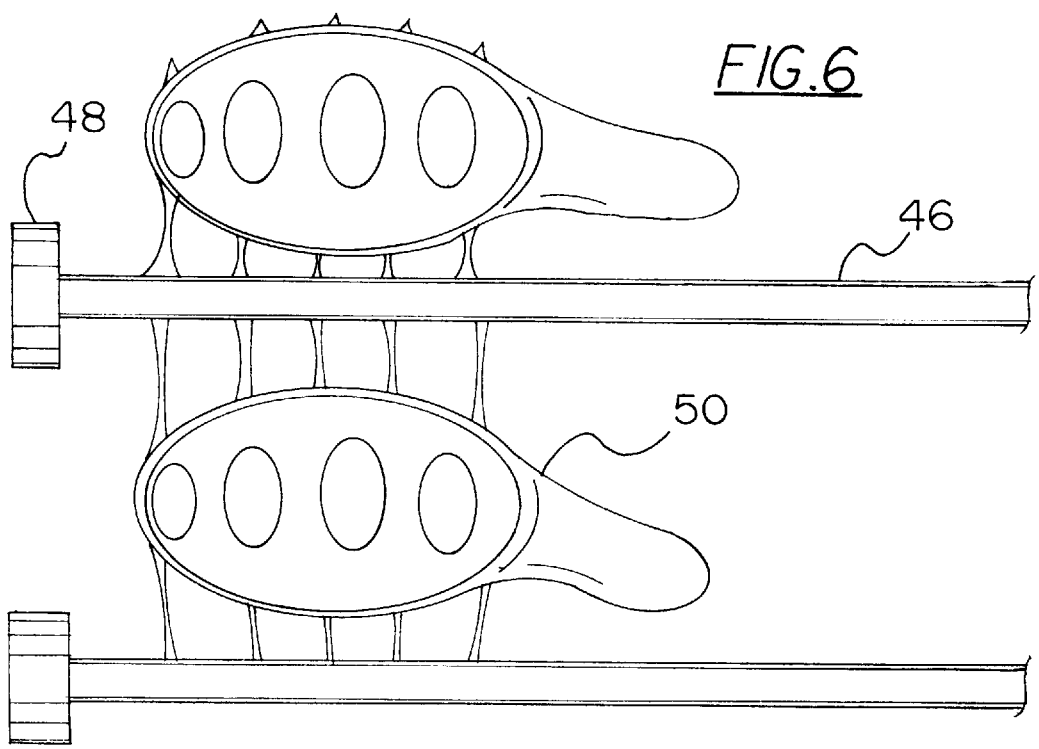
FIG. 6 is a rear view of the coupling between the gloves and the associated rods.
Figure 7:
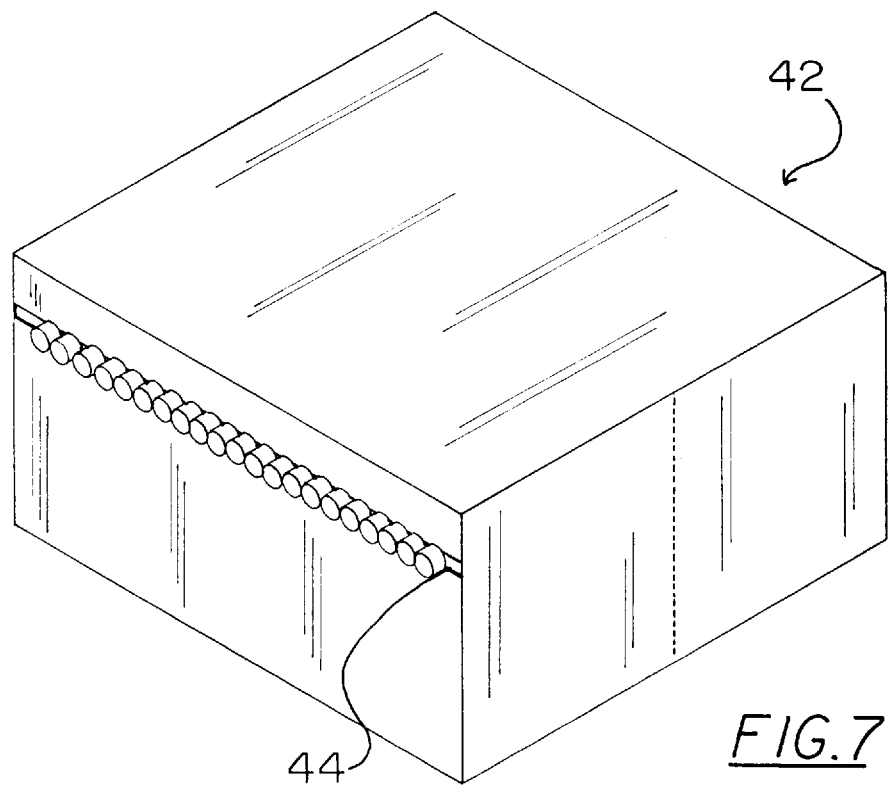
FIG. 7 is a perspective view of the multiple glove dispensing assembly.
Figure 8:
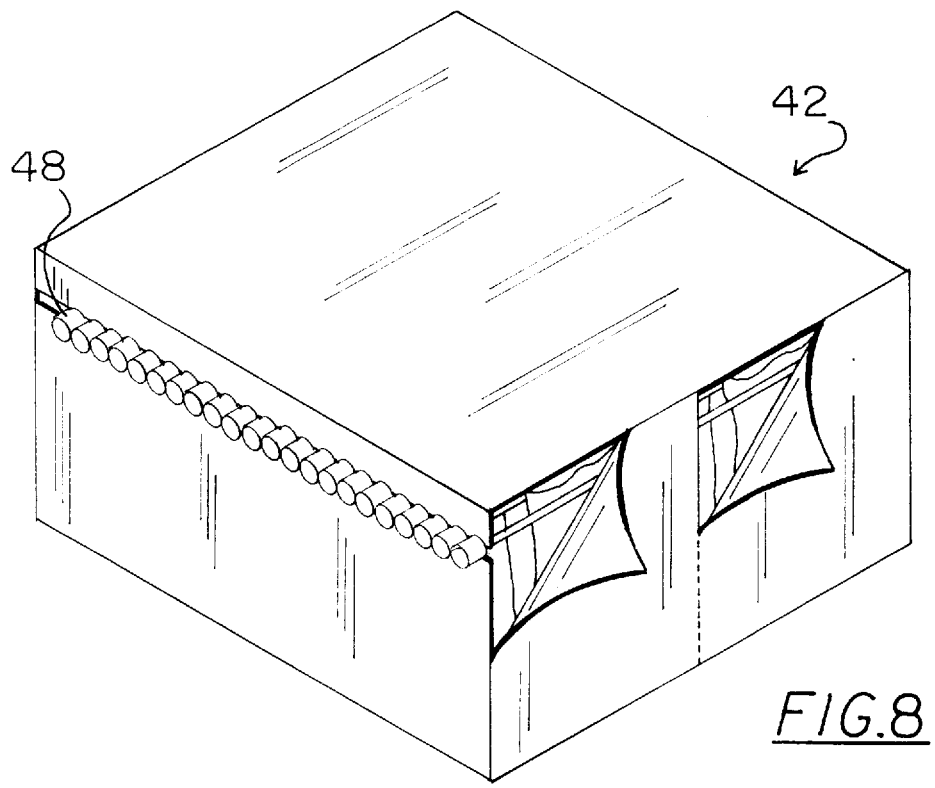
FIG. 8 is another perspective view of the multiple glove dispensing assembly.

As shown in FIGS. 7 & 8, a disposable multiple glove assembly 42 is included with a rectilinear configuration. The disposable multiple glove assembly has a top face, a front face, a rear face, and a pair of side faces defining an interior space with a bottom opening. The side faces have a pair of slots 44 formed therein adjacent the front face of the assembly. As shown in FIGS. 5 and 6, the disposable multiple glove assembly further includes a plurality of rods 46 extending between the slots of the assembly. For precluding lateral movement of the rods within the slots, each is equipped with a cylindrical flange 48 on both ends thereof. The disposable multiple glove assembly further includes a pair of gloves 50 releasably coupled adjacent an opening thereof between each rod. Such coupling preferably comprises a plurality of strands of elastomeric material similar to that which the gloves are constructed from. See FIG. 6. Optionally, at least one fingertip of each glove may be releasably coupled to associated finger tips of a pair of adjacent gloves.

By this design, the disposable multiple glove assembly may be inserted within the upper compartment of the housing with the flanges of the rods residing within the vertical slots of the upper compartment. As shown in FIG. 1, a pair of guards 51 may be included to preclude interference with the sliding of the rods within the slots and further keep the upper compartment sealed. To ensure that the disposable multiple glove assembly is sealed during shipping, the bottom opening ideally has a removable covering secured thereto.

Figure 4:
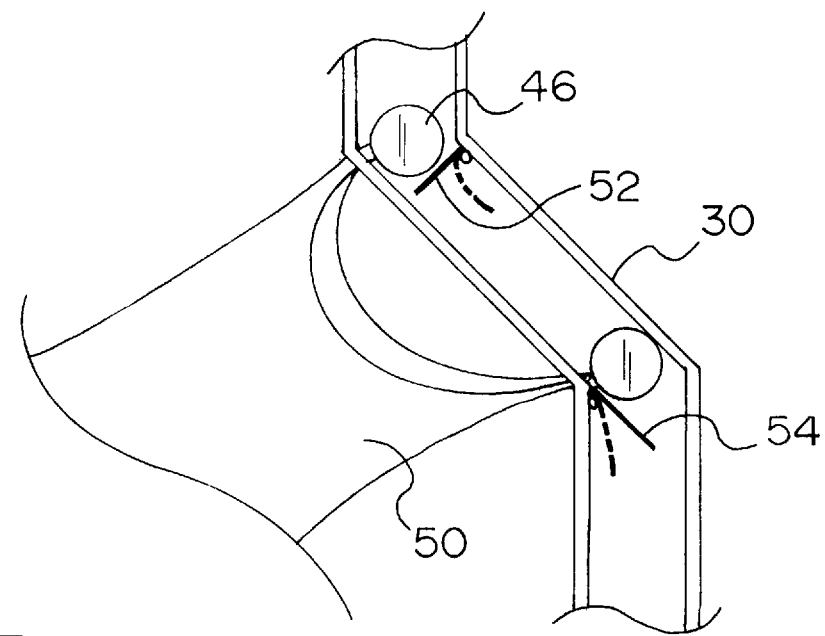
FIG. 4 is a close up view of the section encircled in FIG. 2.

Finally, a dispensing mechanism is provided for allowing the gloves to be dispensed. As best shown in FIG. 4, the dispensing mechanism includes a first flexible tab 52 coupled at a first end thereof to the peripheral lip of the first divider. The first flexible tab extends inwardly therefrom between a bottom of the vertical slots of the upper compartment of the housing. In operation, the first flexible tab is adapted be biased downwardly. Also, it is imperative that the first flexible tab be designed such that a force greater than that afforded by the weight of the rods is required to effect the biasing thereof. The dispensing mechanism further includes a second flexible tab 54 coupled at a first end thereof to the plate of the second divider adjacent the horizontal slot thereof. Such second divider extends from the point of coupling to a position between a bottom of the angled slots of the intermediate compartment of the housing. The second flexible tab is adapted be biased only downwardly in use. Also, it is imperative that the second flexible tab be designed such that it may be biased merely by the force afforded by the weight of a rod. It should be noted that complimenting flexible tabs, as shown in FIG. 3, may be utilized to function similarly with respect to the first and second flexible tabs.

By this structure, a lowermost rod of the disposable multiple glove assembly may be situated below the second flexible tab before use. Further, a second lowermost rod may be situated above the lowermost rod and above the first tab such that the openings of the associated pair of gloves are positioned in alignment with the second ends of the guide tubes. It should be noted that the guide tubes are equipped with cutouts so as not to interfere with the movement of the gloves within the intermediate compartment. If the finger tips of the glove are coupled to those of an above glove, the glove which is ready to be dispensed will be situated essentially horizontally.

In operation, a pair of hands of a user may be inserted within the gloves with a force which first compels the second lowermost rod to bias the first flexible tab thereby allowing it to enter the angled slots. It should be noted that the lowermost rod is prevented from entering the angled slots. The second lowermost rod continues to descend through the angle slots until it abuts the arms of the user whereat the continued force applied by the user releases the coupling between the gloves and the lowermost rod and second lowermost rod. At this point, the lowermost rod enters the lower compartment and, after the removal of the hands of the user, the second lowermost rod falls below the second flexible tab thereby opening another glove to be dispensed. It should be noted that the rods may be removed from the lower compartment for reuse.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved glove dispenser comprising, in combination:

a glove dispensing housing with a rectilinear configuration having a front face, a rear face, a bottom face, a top opening, and a pair of side faces defining an interior space, the housing further having a first divider comprising an inner peripheral lip extending inwardly from the front face, the rear face, and the side faces of the housing and further subdividing the interior space of the housing and defining an upper compartment, the upper compartment having a pair of aligned vertical slots formed in the side faces of the housing adjacent the front face thereof, the housing further having a second divider comprising a planar horizontally oriented plate situated below the first divider thus subdividing the interior space and defining an intermediate compartment between the first divider and the second divider and further defining a lower compartment situated between the second divider and the bottom face of the housing, the intermediate compartment having a pair of angled slots formed in the side faces of the housing wherein the angle slots are in communication at a top end thereof to the vertical slots, a horizontal slot formed in the second divider between the angled slots, a pair of circular cut outs formed in the front face of the housing and oriented side by side, and a pair of horizontally oriented guide tubes integrally coupled to the housing such that each tube has a first opening situated coincidentally in axial alignment with an associated circular cut out and a second opening situated in communication with the intermediate compartment, each guide tube having a slot formed about a periphery thereof in constant alignment with the angle slots of the intermediate compartment, the lower compartment having a pair of aligned rectangular cut outs formed in opposite side faces of the housing adjacent the bottom face thereof, wherein the rectangular cut outs are in communication with a bottom end of both of the angled slots of the intermediate compartment;

a disposable multiple glove assembly with a rectilinear configuration having a top face, a front face, a rear face, and a pair of side faces defining an interior space with a bottom opening, the side faces having a pair of vertical slots formed therein adjacent the front face of the assembly, the disposable multiple glove assembly further including a plurality of rods extending between the slots of the assembly each with a flange on both ends thereof for precluding lateral movement thereof within the slots, the disposable multiple glove assembly further including a pair of gloves releasably coupled adjacent an opening thereof between each rod, whereby the disposable multiple glove assembly may be inserted within the upper compartment of the housing with the flanges of the rods residing within the vertical slots of the upper compartment; and a dispensing mechanism including a first flexible tab coupled at a first end thereof to the peripheral lip of the first divider and extended inwardly therefrom between a bottom of the vertical slots of the upper compartment of the housing, the first flexible tab adapted be biased downwardly, the dispensing mechanism further including a second flexible tab coupled at a first end thereof to the plate of the second divider adjacent the horizontal slot thereof and extended therefrom between a bottom of the angled slots of the intermediate compartment of the housing, the second flexible tab adapted be biased only downwardly, whereby a lowermost rod of the disposable multiple glove assembly may be situated below the second flexible tab and a second lowermost rod may be situated above the first tab such that the openings of the associated pair of gloves are positioned in alignment with the second ends of the guide tubes;

whereby a pair of hands of a user may be inserted within the gloves with a force which first compels the second lowermost rod to bias the first flexible tab thereby allowing it to enter the angled slots and further abut arms of the user whereat the force releases the coupling between the gloves and the lowermost rod and second lowermost rod thereby allowing the lowermost rod to enter the lower compartment and further allowing the second lowermost rod to reside beneath the second flexible tab and another glove to be situated to be dispensed.

2. A glove dispenser comprising:

a glove dispensing housing;

a plurality of rods extending between side faces of the housing;

a pair of gloves releasably coupled adjacent an opening thereof between each rod; and a dispensing means coupled to the housing for allowing the dispensing of the gloves.

3. A glove dispenser as set forth in claim 2 wherein the housing has a rectilinear configuration having a front face, a rear face, a bottom face, a top opening, and a pair of side faces defining an interior space, the housing further having a first divider comprising an inner peripheral lip extending inwardly from the front face, the rear face, and the side faces of the housing and further subdividing the interior space of the housing and defining an upper compartment, the upper compartment having a pair of aligned vertical slots formed in the side faces of the housing adjacent the front face thereof, the housing further having a second divider comprising a planar horizontally oriented plate situated below the first divider thus subdividing the interior space and defining an intermediate compartment between the first divider and the second divider and further defining a lower compartment situated between the second divider and the bottom face of the housing, the intermediate compartment having a pair of angled slots formed in the side faces of the housing wherein the angle slots are in communication at a top end thereof to the vertical slots, a horizontal slot formed in the second divider between the angled slots, a pair of circular cut outs formed in the front face of the housing and oriented side by side, and a pair of horizontally oriented guide tubes integrally coupled to the housing such that each tube has a first opening situated coincidentally in axial alignment with an associated circular cut out and a second opening situated in communication with the intermediate compartment, each guide tube having a slot formed about a periphery thereof in constant alignment with the angle slots of the intermediate compartment, the lower compartment having a pair of aligned rectangular cut outs formed in opposite side faces of the housing adjacent the bottom face thereof, wherein the rectangular cut outs are in communication with a bottom end of both of the angled slots of the intermediate compartment.

4. A glove dispenser as set forth in claim 3 wherein the rods are situated within a disposable multiple glove assembly with a rectilinear configuration having a top face, a front face, a rear face, and a pair of side faces defining an interior space with a bottom opening, the side faces having a pair of vertical slots formed therein adjacent the front face of the assembly, whereby the disposable multiple glove assembly may be inserted within the upper compartment of the housing with the flanges of the rods residing within the vertical slots of the upper compartment.

5. A glove dispenser as set forth in claim 4 wherein the dispensing means includes a first flexible tab coupled at a first end thereof to the peripheral lip of the first divider and extended inwardly therefrom between a bottom of the vertical slots of the upper compartment of the housing, the first flexible tab adapted be biased downwardly, the dispensing mechanism further including a second flexible tab coupled at a first end thereof to the plate of the second divider adjacent the horizontal slot thereof and extended therefrom between a bottom of the angled slots of the intermediate compartment of the housing, the second flexible tab adapted be biased only downwardly, whereby a lowermost rod of the disposable multiple glove assembly may be situated below the second flexible tab and a second lowermost rod may be situated above the first tab such that the openings of the associated pair of gloves are positioned in alignment with the second ends of the guide tubes.

6. A glove dispenser comprising:

a glove dispensing housing;

a plurality of gloves releasably fixed in relation to each other adjacent an opening thereof; and a dispensing means coupled to the housing for maintaining the openings of the gloves in an open orientation thereby allowing the dispensing of the gloves, the dispensing means includes a first flexible tab coupled at a first end thereof to the housing, the first flexible tab adapted to be biased downwardly, the dispensing means further including a second flexible tab coupled at a second end thereof to the housing, the second flexible tab adapted to be biased only downwardly, whereby a lowermost rod may be situated below the second flexible tab and a second lowermost rod may be situated above the first tab such that the openings of the associated pair of gloves are positioned in alignment with openings in the housing.

* * * * *